(12) United States Patent
Berde et al.

(10) Patent No.: US 7,725,972 B2
(45) Date of Patent: Jun. 1, 2010

(54) TOOTHBRUSH

(75) Inventors: Tamas Berde, Buehl (DE); Christoph Geiberger, Königswinter (DE); Ralph Francis Walker, Brentford (GB)

(73) Assignee: GlaxoSmithKLine Consumer GmbH & Co. KG, Buehl (Baden) (DE)

( * ) Notice: Subject to any disclaimer, the term of this patent is extended or adjusted under 35 U.S.C. 154(b) by 1349 days.

(21) Appl. No.: 10/496,210

(22) PCT Filed: Nov. 18, 2002

(86) PCT No.: PCT/EP02/12879

§ 371 (c)(1), (2), (4) Date: Apr. 21, 2005

(87) PCT Pub. No.: WO03/043459

PCT Pub. Date: May 30, 2003

(65) Prior Publication Data

US 2005/0198753 A1    Sep. 15, 2005

(30) Foreign Application Priority Data

Nov. 20, 2001  (GB) .................................. 0127799.5
Jan. 16, 2002  (GB) .................................. 0200870.4
May 2, 2002    (GB) .................................. 0210137.6

(51) Int. Cl.
  *A61C 17/22*  (2006.01)
  *A61C 17/34*  (2006.01)

(52) U.S. Cl. .............................. 15/22.1; 15/22.2; 15/28

(58) Field of Classification Search ................. 15/22.1, 15/28, 22.2
See application file for complete search history.

(56) References Cited

U.S. PATENT DOCUMENTS

| | | | |
|---|---|---|---|
| 4,128,910 A | | 12/1978 | Iada |
| 4,277,862 A | | 7/1981 | Weidemann |
| 4,288,883 A | | 9/1981 | Dollinsky |
| 5,040,260 A | | 8/1991 | Michaels |
| 5,120,225 A | | 6/1992 | Amit |
| 5,524,312 A | | 6/1996 | Tan et al. |
| 5,732,433 A | | 3/1998 | Droessler et al. |
| 5,850,655 A | * | 12/1998 | Gocking et al. ............... 15/28 |
| 6,000,083 A | | 12/1999 | Nottingham et al. |
| 6,510,575 B2 | * | 1/2003 | Calabrese ................... 15/22.1 |
| 6,725,490 B2 | * | 4/2004 | Blaustein et al. ............. 15/22.2 |

FOREIGN PATENT DOCUMENTS

| | | | |
|---|---|---|---|
| EP | 0360766 | | 3/1990 |
| EP | 0435329 | | 7/1991 |
| EP | 0990424 | | 4/2000 |
| EP | 1132057 | | 9/2001 |
| GB | 214701 | | 4/1924 |
| GB | 2040161 | | 8/1980 |
| GB | 2214420 | | 9/1989 |
| JP | 5-146313 | * | 6/1993 |

(Continued)

*Primary Examiner*—Randall Chin
(74) *Attorney, Agent, or Firm*—Nora Stein-Fernandez; Theodore R. Furman

(57) ABSTRACT

A head for an electric toothbrush having first and second brush parts, one of which is rotary and the other is reciprocally moveable or static. Preferred forms have elastomeric oral hygiene parts, and electric toothbrush heads with novel "V" sectioned oral hygiene parts are also disclosed.

6 Claims, 5 Drawing Sheets

FOREIGN PATENT DOCUMENTS

| | | |
|---|---|---|
| WO | WO96/15696 | 5/1996 |
| WO | WO96/28994 | 9/1996 |
| WO | WO97/16995 | 5/1997 |
| WO | WO98/18364 | 5/1998 |
| WO | WO99/37181 | 7/1999 |
| WO | WO00/49911 | 8/2000 |
| WO | WO00/64307 | 11/2000 |
| WO | WO00/76369 | 12/2000 |
| WO | WO 0101817 | 1/2001 |
| WO | WO01/21036 | 3/2001 |

* cited by examiner

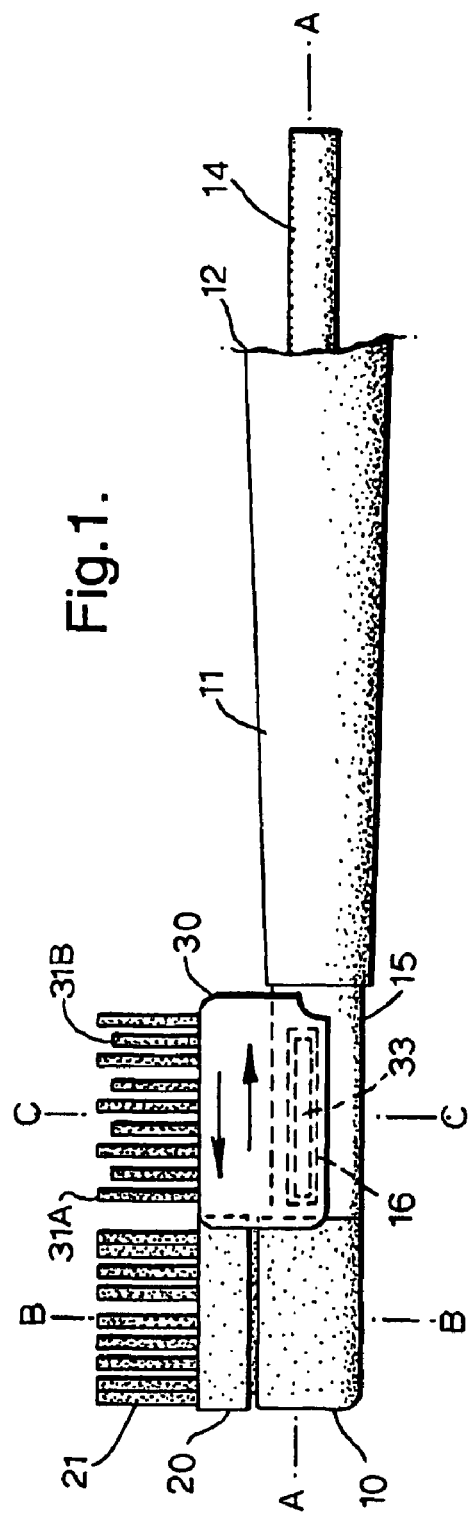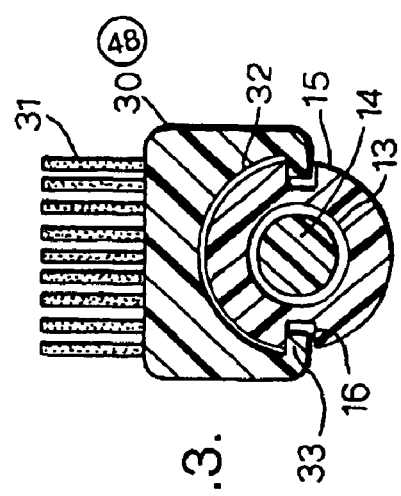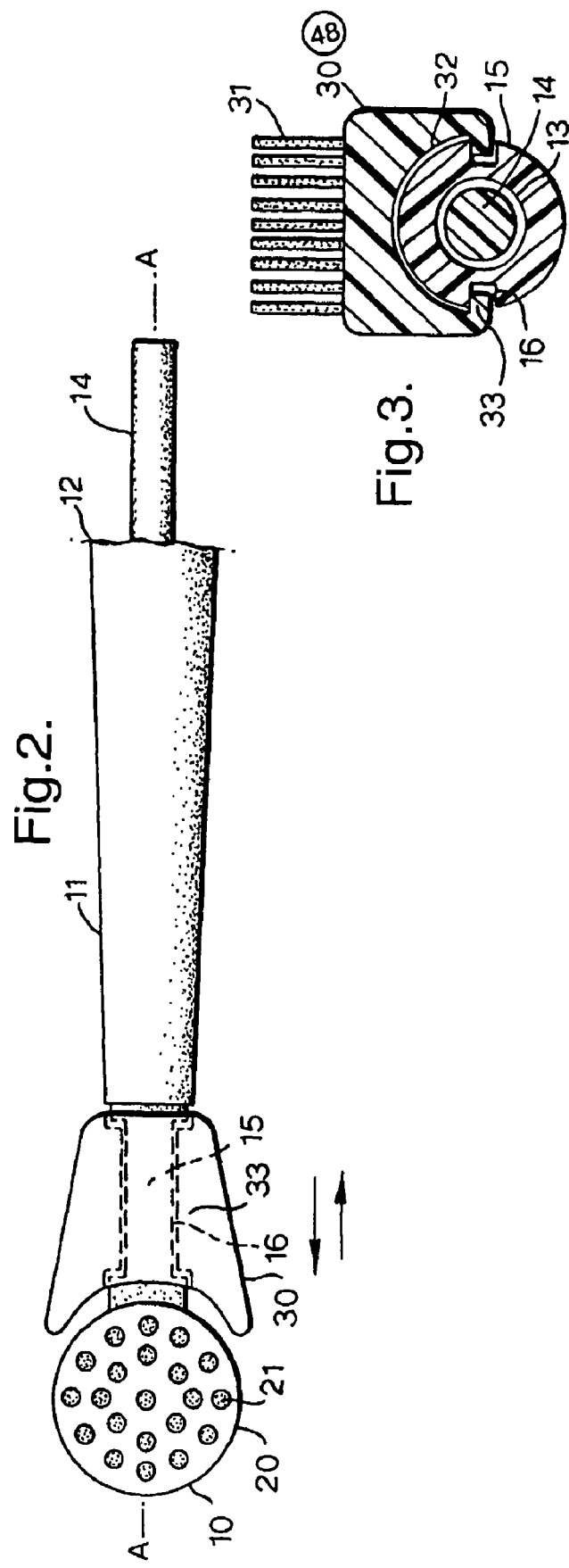

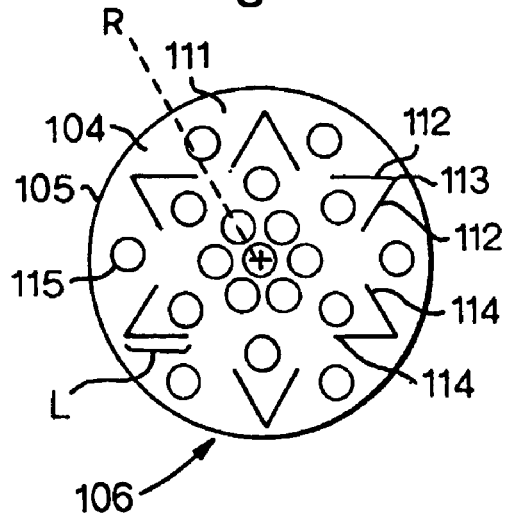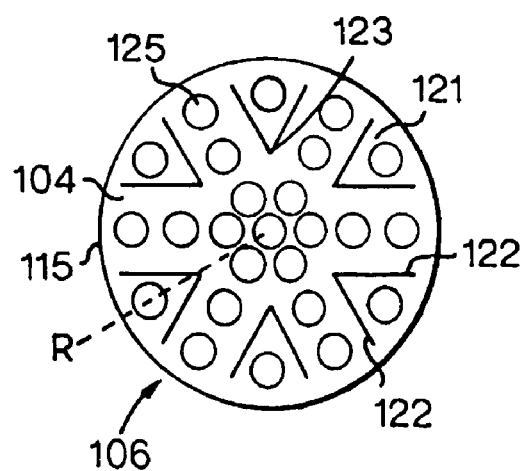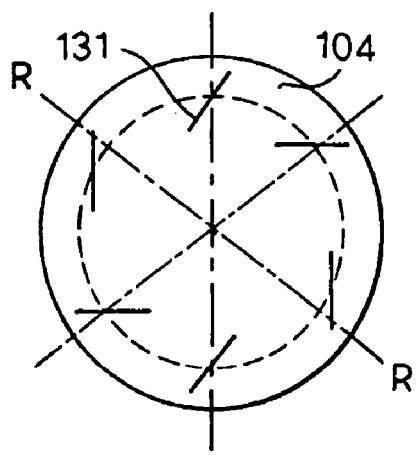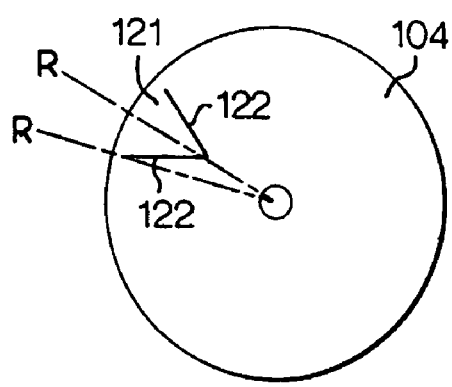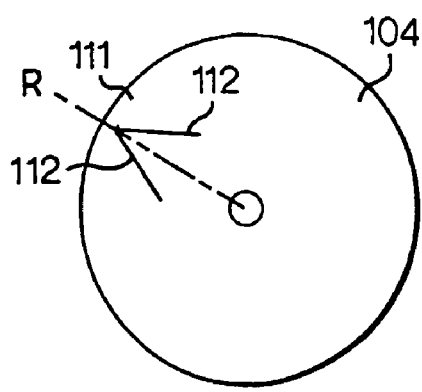

TOOTHBRUSH

TITLE OF THE INVENTION

This application claims the benefit of International Application Number PCT/EP02/12879 filed Nov. 18, 2002.

This invention relates to toothbrushes, in particular to electric toothbrushes, specifically to a brush head suitable for an electric toothbrush.

BACKGROUND OF THE INVENTION

Electric toothbrushes generally comprise a handle which contains inter alia a power supply and a drive motor, and a head which includes one or more brush part bearing oral hygiene parts to be driven by the motor, generally in rotary motion about a rotation axis transverse to the head—handle direction, and connected by a transmission means to the motor. The term "oral hygiene part" as used herein refers to a part which contributes to oral hygiene, for example by cleaning the teeth, gums or other oral tissues, and/or polishing the teeth, and/or massaging the gums or other oral tissues. Often there is a neck between the handle and the head, and containing such a transmission means e.g. a drive shaft. Often the head is replaceable, typically being either replaceably connectable to the end of the neck remote from the handle, or being integral with the neck and the neck being replaceably connectable to the handle at its end remote from the head.

Often the rotary motion is oscillatory, i.e. motion involving reciprocal angular displacement about a mean position. Sometimes the rotary motion also involves a reciprocal back and forth movement of the brush part along the rotational axis direction.

Numerous constructions of electric toothbrush are known, for example the applicant's own Dr BEST "E-FLEX" (™) electric toothbrush launched in 2000 which has a brush part mounted for oscillatory rotary motion. U.S. Pat. No. 6,000,083 discloses an electric toothbrush having both rotating and static i.e. non rotating brush parts.

It is known from EP-A-0 990 424 (Procter & Gamble) to provide an electric toothbrush having a motor-driven first brush part and a second brush part which is static, i.e. integrally made with the head and immovable relative to the head. It is also known from EP-A-1 132 057 (Unilever) to provide an electric toothbrush having bristle-bearing segments linked flexibly to the head by means of a leaf hinge of a plastic material integral with the head.

Very often the oral hygiene parts comprise plural bristles arranged in discrete tufts or mats on a surface of the brush part. Typically such bristles are made of a nylon polymer e.g. the well known Tynex™. Often bristles are the only oral hygiene parts of a toothbrush. Toothbrushes having elastomeric oral hygiene parts on their head to contact the teeth and gums are known.

Numerous types of elastomeric oral hygiene parts are known. GB-A-2 040 161 discloses longitudinally extending elastomer strips. GB-A-2 214 420 and WO-A-00/49911 both disclose a toothbrush having a head from which project small rubber pyramids. GB-A-214 701 discloses a toothbrush having oral hygiene parts comprised of strips of crepe rubber, in one theoretically discussed embodiment of which the strips may have bristles sandwiched between the strips of crepe rubber. EP-A-0 360 766 discloses small rubber cylinders with knobbed ends. U.S. Pat. No. A-4,128,910 discloses a toothbrush having rubber oral hygiene parts of various pyramid and ridge shapes. U.S. Pat. No. A-4,277,862 discloses a toothbrush having resilient gum massage parts along the outer edges of the bristle pattern. U.S. Pat. No. A-4,288,883 discloses rubber cones. U.S. Pat. No. 5,040,260 discloses a toothbrush having a head from which extend small rubber cones. WO-A-96/15696 discloses a toothbrush head provided with strips of a flexible and resilient material, typically a non-elastomeric nylon material, and typically aligned either perpendicular to or parallel to the longitudinal direction. WO-A-96/28994 discloses elastomer bars extending perpendicular to the longitudinal direction and parallel to the edges of the head in combination with bristle "bars" having an elongate cross section cut across the bristle direction, and also discloses a curved rubber "scooping bar" at the tip end of the head. WO-A-97/16995 discloses elastomer "bristles". WO-A-98/18364 discloses tooth polishing pads or finger-like structures. WO-A-99/37181 discloses an outer ring of rubber fingers surrounding an inner dense pack of bristles. WO-A-00/64307 discloses rubber bars with a generally triangular cross section. WO-A-00/76369 discloses elastomeric massaging parts with rotational symmetry through an angle of 120° or less e.g. cylinders. WO-A-01/21036 discloses a longitudinally extending elastomeric wall-like member running for at least half the length of the head.

Electric toothbrushes having elastomeric oral hygiene parts are known, e.g. WO-A-01/01817 discloses an electric toothbrush having a head with elastomeric fingers or arcuate lamellae mounted on it. EP-A-0 435 329 discloses an electric toothbrush having interdental points in rubber mounted on it.

SUMMARY OF THE INVENTION

It is an object of this invention to provide an electric toothbrush having improved ability to clean the teeth, particularly to adjust itself to a user's teeth. For example each user is likely to have a different spacing of interdental gaps between his/her teeth and it is desirable for an electric toothbrush to be able to accommodate itself to any pattern of interdental gaps. It is a further object of this invention to provide an improved electric toothbrush having elastomeric oral cleaning parts on its head.

In a first embodiment this invention provides a head for an electric toothbrush which is connected to, or replaceably connectable to, a handle which contains an electric motor, to provide a toothbrush having a head-handle longitudinal direction, characterised in that the head has:

at least one first brush part bearing oral hygiene parts and which is driveable by the motor in rotary motion about a first rotation axis generally perpendicular to the longitudinal direction;

and at least one second brush part bearing oral hygiene parts, which is not driven by the motor and is capable of limited reciprocal longitudinal motion, or limited reciprocal motion along a direction generally perpendicular to both the longitudinal direction and to the first rotation axis, or limited reciprocal rotary motion about a second rotation axis generally parallel to the first rotation axis.

In this first embodiment the oral hygiene parts may be exclusively bristles.

Alternatively in this first embodiment at least one of the first or second brush parts has oral hygiene parts being bristles mounted thereon, and at least one of the first or second brush parts has one or more elastomeric oral hygiene part mounted thereon.

It is considered that an electric toothbrush head construction having first and second brush parts, one of which is driveable by an electric motor and is mounted on the head for rotation, and the other is static i.e. imoveable relative to the head, at least one of the brush parts being provided with elastomeric oral hygiene parts is also novel.

Therefore in a second embodiment this invention provides a head for an electric toothbrush which is connected to, or replaceably connectable to, a handle which contains an electric motor, to provide a toothbrush having a head-handle longitudinal direction, characterised in that the head comprises first and second brush parts, at least one of the first or second brush parts being driveable by the motor in rotary motion about a first rotation axis generally perpendicular to the longitudinal direction, the other of the first or second brush parts being static, at least one of the first or second brush parts having bristles mounted thereon, at least one of the first or second brush parts having one or more elastomeric oral hygiene part mounted thereon.

DETAILED DESCRIPTION OF THE INVENTION

The term "head" as used herein comprises the bristle-bearing part of the toothbrush. Generally the head will extend integrally toward the handle as a neck. Generally the head will include a suitable mounting for a brush part which is mounted or mountable on the head for rotation, or for limited reciprocal motion (in those embodiments of this invention which include such a brush part).

The term "elastomeric" as used herein includes both natural rubbers and synthetic elastomer materials, preferably thermoplastic elastomer materials. Preferably the elastomeric material has a hardness from about 10 to about 90 Shore A, more preferably 50 Shore A or less, e.g. from about 14 to about 35 Shore A. Suitable elastomeric polymers include styrenes (for example styrene ethylene butadiene styrene, or styrene butadiene styrene), and silicone elastomeric materials may also be used. Suitable elastomeric materials include those available under the trade names Megol and Santoprene. Manual (i.e. non-powered) toothbrushes are known with elastomeric oral hygiene parts, and the elastomeric materials used for these are likely to be suitable for the elastomeric oral hygiene parts of the toothbrush heads of this invention.

Preferably in both the first and second embodiment there is only one first brush part and only one second brush part.

Preferably in both the first and second embodiment the first and second brush parts are relatively longitudinally disposed along the head-handle direction.

Preferably in both the first and second embodiment there is a first brush part furthest from the handle, and a second brush part adjacent to the first brush part and closer to the handle (in the assembled toothbrush) than the first brush part.

Preferably in both the first and second embodiment a first brush part furthest from the handle is mounted or mountable for rotation on the head about a rotation axis perpendicular to the head-handle direction. Such a first brush part may be mounted for rotation in an otherwise conventional manner, and may be driven in rotational motion in a conventional manner via a motor. Such a motor-driven first brush part is suitably circular about the first rotation axis, and suitably the rotary motion of the first brush part is limited reciprocal rotary motion.

The term "rotary motion" used herein includes limited reciprocal rotary motion, i.e. rotary motion through an angle less than 360° in a first rotary direction, followed by rotary motion through the same angle as the opposite rotary direction. Suitably the angle is less than 180°, preferably less than 90°.

Preferably in both the first and second embodiments only one of the first or second brush parts is mounted for rotation, especially a first brush part at the end of the head remote from the handle.

Preferably in the first embodiment the second brush part, preferably a second brush part longitudinally adjacent to this first brush part and closer to the handle, is capable of limited reciprocal longitudinal motion.

A second brush part may be enabled to perform limited reciprocal motion by means of end-stop abutment parts on respectively the head and on the second brush part, which abut when the second brush part reaches the ends of its limited reciprocal motion, to thereby limit the reciprocal motion.

For example when the second brush part performs limited reciprocal longitudinal motion the head may comprise a rail part along which the second brush part may slideably longitudinally move, and the second brush part may have one or more part, e.g. a pin or slider which can move longitudinally along one or more corresponding guide, slot or groove in the head e.g. in the rail part, the opposite longitudinal ends of the guide, slot or groove comprising the end-stop means. In a preferred construction the second brush part has pins or sliders on opposite longitudinal sides which slideably engage in respective longitudinal guides, grooves or slots in opposite sides of the head. For example the second brush part may comprise a saddle of substantially "C" shaped cross section across the longitudinal direction which an sit longitudinally slideably upon the head, and the ends of the "C" comprise sliders, which slideably engage in respective longitudinal guides, grooves or slots in opposite sides of the head. By making the second brush part, or at least such pins or sliders resilient, e.g. of a resilient plastics material such as polypropylene, polystyrene etc. and of suitable dimensions which will be apparent to those skilled in the art, such a "C" sectioned structure can snap fit into the slots and be retained on the head.

In an alternative construction for example the second brush part may have a longitudinal channel which can run along a longitudinal rail part of the head, for example threaded longitudinally through the channel. Such a rail part and channel may have end-stop abutment parts to permit limited longitudinal relative movement of the second brush part and head part.

Similarly when the second brush part is constructed to perform limited reciprocal motion in a direction generally perpendicular to the longitudinal direction the second brush part and head part may have a similar pin or slider and slot or groove, or a channel and rail part, but aligned generally perpendicular to the longitudinal direction, with end-stop means analogous to those described above.

Preferably in the second embodiment the static second brush part may be made integrally with the head.

Preferably in both the first and second embodiments both of the first and second brush parts have bristles mounted thereon, extending from a bristle face thereof. At least one of the first and second brush parts, of either of the first and second embodiments, may (and in the case of the second embodiment does) have at least one elastomeric oral hygiene element thereon. In a preferred construction a first brush part mounted for rotation and furthest from the handle has bristles but no elastomeric cleaning parts mounted thereon, and a second brush part closer to the handle has both bristles and elastomeric cleaning parts mounted thereon.

Bristles on the first and/or second brush parts may extend generally perpendicular to the longitudinal direction and to the bristle face. Alternatively the bristles may be aligned at a non-perpendicular angle to the surface of the brush part from which they extend, e.g. non perpendicular relative to the longitudinal direction, e.g. leaning toward or away from the handle. On a first brush part mounted for rotation the tufts of bristles may lean in a manner as disclosed in PCT/EP01/14040 the contents of which are incorporated herein by reference. For example widthways separated tufts of bristles, especially on a non-rotating second brush part, may lean in respective opposite such directions so that as seen looking widthways the widthways separated tufts are seen to cross e.g. in an 'X' shape. Such a bristle arrangement is well known, e.g. from inter alia U.S. Pat. No. 3,085,273 and U.S. Pat. No. 5,274,873 etc. The bristles may all be the same length, or tufts may differ in length, for example longitudinally adjacent tufts alternating between two different relatively longer and relatively shorter lengths, for example as disclosed in DE-A-44 09 395.

The one or more elastomeric oral hygiene part may be of known type, for example as disclosed in the art discussed above, e.g. one or more of the known small rubber cones, small rubber pyramids, strips of rubber, elastomer "bristles", tooth polishing pads, finger-like structures, elastomer bars e.g. of a generally rectangular cross section, elastomeric massaging parts with rotational symmetry through an angle of 120° or less, cylinders, a resilient elastomer wall-like member, small rubber cylinders with knobbed ends, elastomeric fingers or arcuate lamellae, interdental points in rubber etc.

A preferred type of elastomeric oral hygiene part comprises an elastomeric strip extending in its length dimension from the brush part, particularly from a second brush part closer to the handle than a first brush part, having a width dimension perpendicular to its length direction, and a thickness dimension perpendicular to both the length and width directions, the thickness dimension being less than the width dimension. Typically the length of such a strip may be generally the same as or less than the length of conventional toothbrush bristles, the width may be in the range ca. 0.1-0.25 of the length dimension, and the thickness dimension may be ca. 0.1-0.25 of the width dimension.

The width direction of such one or more strip may be aligned perpendicular or parallel to the head-handle direction, or may be aligned at a non-zero, non-perpendicular angle to the handle-head direction and such an alignment may be either so that the edge of the strip closest to the handle is inward or outward relative to the opposite edge. If a plurality of such strips is present, then the strips may be aligned at a variety of angles to the head-handle direction.

A preferred embodiment of such strips is for a pair of such strips to be adjacent, preferably longitudinally adjacent, and for such adjacent strips to converge such that their respective width dimensions form a "V" shape. In a particularly preferred embodiment a pair of such adjacent, preferably longitudinally adjacent, strips is integrally formed as an integral strip of a "V" shaped cross section as cut across their length direction. The point of such a "V" may point outwardly or preferably inwardly relative to the longitudinal head-handle. Typically the "V" may enclose an angle of 45°-90°, e.g. 55°-65°.

The one or more elastomeric oral hygiene part may be positioned anywhere on the first and/or second brush part, but preferably around the sideways edges of a head part, e.g. a second brush part, so that it/they can massage the gums. It is preferred that plural elastomeric oral hygiene parts are arranged along each of the sideways edges of a second brush part which is closer to the handle than a first brush part. It is particularly preferred that plural of the above-mentioned "V" sectioned elastomeric oral hygiene parts are positioned around each edge of a second brush part.

A particularly preferred form of the toothbrush head of the first embodiment of this invention therefore comprises:

a first brush part furthest from the handle mounted or mountable on the head for rotation about a rotation axis perpendicular to the head-handle direction, a second brush part longitudinally adjacent to this first brush part and closer to the handle, which is capable of limited reciprocal longitudinal motion, the first and second brush part having oral hygiene parts comprising bristles mounted thereon.

Another particularly preferred form of the toothbrush head of the first embodiment of this invention therefore comprises:

a first brush part furthest from the handle mounted or mountable on the head for rotation about a rotation axis perpendicular to the head-handle direction, a second brush part longitudinally adjacent to this first brush part and closer to the handle, which is capable of limited reciprocal longitudinal motion, the first and second brush part having oral hygiene parts comprising bristles mounted thereon, and the second brush part having both bristles and at least one elastomeric cleaning part mounted thereon, the elastomeric oral hygiene part comprising an adjacent pair of elastomeric strips with their width directions converging to define a "V" shaped cross section between them as cut across the length direction, the point of the "V" pointing inwardly relative to the longitudinal head-handle direction.

In this preferred form of the first embodiment of the toothbrush of the invention the plural elastomeric strips are preferably positioned around the edge of the second brush part.

The elastomeric oral hygiene part(s), e.g. such strips of elastomeric material, may extend to the edge of the brush part, and preferably slightly beyond. The elastomeric material of the oral hygiene part(s) parts may be continued around the edge of the brush part and down the sides of the brush part for example to provide gum massaging parts or a buffer against excessive impact with the oral tissues, especially with the buccal surfaces.

It is believed to be novel to provide an electric toothbrush head with an elastomeric oral hygiene part of the above-described type comprising a pair of elastomer strips converging such that their respective width dimensions form a "V" shape, e.g. integrally formed as an integral strip of a "V" shaped cross section as cut across their length direction. Such a head comprises a third embodiment of this invention.

For example such a head of this third embodiment may comprise a head for an electric toothbrush which is connected to, or replaceably connectable to, a handle which contains an electric motor, to provide a toothbrush having a head-handle longitudinal direction, the head having at least one brush part bearing at least one oral hygiene part and which is driveable by the motor in rotary motion about a rotation axis generally perpendicular to the longitudinal direction characterised in that:

the brush part carries an oral hygiene part comprising an elastomeric strip which in section as cut across the rotation axis is elongated along a long dimension which is aligned at a non-zero, non-perpendicular angle to a radius from the rotation axis.

Preferably the elastomeric strip of this third embodiment of the invention extends in a strip length direction which is substantially aligned with the rotation axis.

Preferably the cross section of the elastomeric strip of this third embodiment of the invention is elongated in a straight line, and its section preferably has substantially parallel opposite long sides.

Preferably of this third embodiment of the invention the long dimension of the section is aligned at an angle between 10°-80° to the radius, more preferably between 30°-60°, e.g. ca. 45° to the radius.

Preferably in this third embodiment of the invention the brush part carries plural elastomeric strips, preferably arranged on the circumference of a circle centred on the axis of rotation. There may be one or more such circle, preferably concentric, each having elastomeric strips arranged around it. For example there may be 6-20 such strips, e.g. 10-16.

In a preferred form of this third embodiment of the invention, pairs of the elastomeric strips are arranged such that the alignment of the long dimensions of elastomeric strips adjacent to each converge toward a "V" or chevron shape. Preferably such pairs of elastomeric strips are arranged around a circle centred on the rotation axis. In such an arrangement the point of the "V" or chevron may point, preferably radially, either inwardly toward or outwardly from the axis of rotation. However the point of the "V" or chevron may point around a circle centred on the rotation axis. In a particularly preferred construction the adjacent edges of such converging adjacent elastomeric strips are joined so that the pair of joined elastomeric strips forms a unitary oral hygiene part with a "V" or chevron cross section cut across the rotation axis.

In this third embodiment of the invention the angle between the limbs of the "V" or chevron may typically be in the range 30°-120°, for example 60°-100°. Typically the angle of the "V" or chevron may be symmetrically bisected by a radius from the axis of rotation.

In this third embodiment of the invention typically there may be 5-12 such "V" or chevron sectioned oral hygiene parts on the head.

In the head of this third embodiment of the invention the elastomeric strips may be combined in a cluster, centred on the rotation axis, with other oral hygiene parts such as tufts of bristles. For example there may be plural elastomeric strips of which adjacent pairs are joined to comprise a strip of unitary "V" or chevron cross section, arranged on the circumference of a circle centred on the axis of rotation, surrounding an inner cluster comprising one or more ring or polygon of tufts. For example there may be one or more tuft circumferentially between adjacent strips or the above-mentioned "V" section elements. For example there may be one or more tuft of bristles located in the "bite" of the "V" of such a convergent pair of strips. Suitably the circle of elastomeric strips may be the radially outermost, from the rotation axis, of the cleaning elements for example to enable the elastomeric strips to contact the user's gums.

The elastomeric strip(s) of all embodiments referred to herein may extend from the face of the brush part for a length approximately the same as that of bristles from the head of a conventional electric toothbrush, e.g. typically 8-11 mm, or may extend for a greater or lesser distance than this. The long dimension of each strip, e.g. of each limb of the "V" of a joined adjacent pair, may be ca. 1-3 mm, and the thickness between the long surfaces may for example be 0.1-0.5 mm.

An elastomeric oral hygiene part may be made by a process of injection moulding, in which a hard plastic material part of the brush part is formed first, and then the formed plastic part is enclosed in a mould cavity defining the shape of the elastomeric oral hygiene part(s) to be formed, and the elastomeric material is injected into the mould in a fluid state. Analogous processes to make toothbrushes with elastomeric material parts are well known.

Suitable drive mechanisms to drive the brush part of the toothbrush heads of this invention are known, for example in U.S. Pat. No. 5,577,285 and the drive speeds, amplitudes, and oscillation frequencies, e.g. ca. 3000-6000 rpm achievable by means of such known drive mechanisms are believed to be suitable for the head part of the present invention.

Therefore the invention further provides an electric toothbrush having a head part according to any of the first, second or third embodiments as described above.

The head of this invention may be connectable, preferably replaceably connectable, to a toothbrush handle containing an electric drive motor. For this purpose the head part suitably has connection means by which the head part may be connected to the handle to thereby connect the brush part to the motor. The head part may comprise a hollow neck part longitudinally between the brush part and the handle and enclosing a drive shaft by which the motor can drive the brush part via suitable transmission means, and the end of such a neck part closest to the handle may itself be connectable, preferably replaceably, to the handle in a manner which also connects the drive shaft to the motor. Alternatively the brush part may itself be connectable, preferably replaceably, to the head part at its end remote from the handle. Many alternative connection means, and means by which the motor can drive the shaft and the shaft drive the brush part are known.

The brush part and bristles if present of the head part of this invention may be made of materials which are conventional in the field of electric toothbrush manufacture, e.g. respectively of plastics materials and nylon fibres. The plastics material parts of the bristle brush part and other plastics material parts of the toothbrush may be made by an injection moulding process.

The toothbrush head of this invention is connected to or replaceably connectable to a handle of the toothbrush which contains an electric motor which may be conventional, driven by replaceable, non-replaceable or re-chargeable batteries, and a switch means to active the motor. The motor may be connected to or connectable to the head by means of a conventional drive shaft and transmission unit, passing along a generally longitudinal neck between the handle and body. The head and handle may be integrally permanently connected, and such a toothbrush may be disposable, e.g. once the batteries are drained the whole toothbrush is thrown away. Alternatively the head may be replaceably connectable to the handle by any conventional form of connection such as a bayonet connection. The replaceable connection may be between the head and such a neck, or between such a neck and the handle. Numerous suitable motors, drive shaft and transmission systems, batteries, switches etc. which can produce such rotary or oscillatory rotary motion are known from the literature and from commercially available toothbrushes, see for example U.S. Pat. No. 5,577,285, U.S. Pat. No. 6,000,083, WO-A-01/06947, WO-A-96/37164 etc. The materials of the head, neck and handle of the toothbrush of this invention may be entirely conventional in the field of toothbrush technology. The parts of the toothbrush of this invention may be manufactured and assembled using techniques generally conventional to the art of toothbrush manufacture, e.g. using two-component injection moulding to manufacture plastics material parts and the elastomeric oral hygiene parts.

BRIEF DESCRIPTION OF THE DRAWINGS

The invention will now be described by way of non-limiting example only, with reference to the accompanying drawings which show:

FIG. 1 shows a side view of a head part of a toothbrush of the first embodiment of this invention with occluded parts shown with dotted lines.

FIG. 2 shows a plan view of the head part of FIG. 1 looking down along the first rotation axis, with occluded parts shown with dotted lines.

FIG. 3 shows a cross section through the head part as shown in FIGS. 2 and 3 cut along the line C-C of FIG. 1.

FIG. 11 shows a plan view of a cluster of oral hygiene parts of the toothbrush of FIG. 10

FIG. 12 shows a plan view of an alternative cluster of oral hygiene parts of the toothbrush of FIG. 10

FIGS. 13A, 13B and 13C show the geometric basis of FIGS. 11 and 12.

Referring to FIGS. 1, 2 and 3, a toothbrush head part 10 overall according to the first embodiment of this invention is shown. The head part 10 is integrally made with a neck part 11, which is integrally extended at its end 12 to form an integral handle (not shown). The handle contains a battery-powered electric motor and its batteries, with assembled switch means etc. for the user to operate the toothbrush. The head 10 and handle (not shown) lie along a longitudinal direction (A-A). Longitudinally passing along an internal channel 13 in the neck 11 is a drive shaft 14 by which a first brush part 20 mounted on the head part 10 can be driven by the motor (not shown) within the handle.

Figure 4:
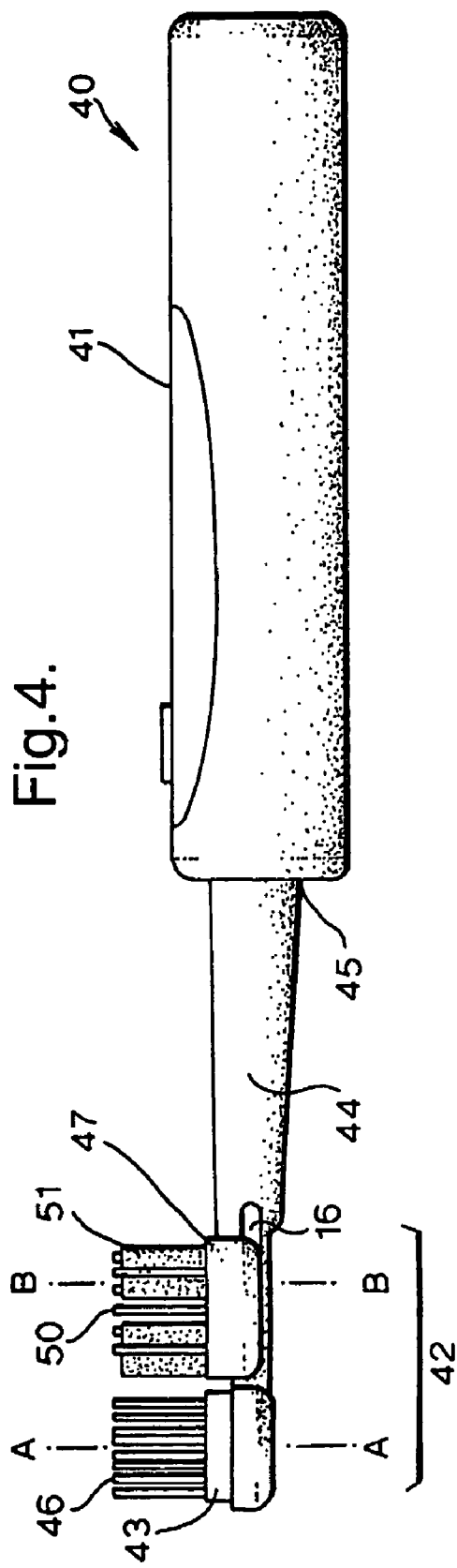
FIG. 4 shows a schematic overall side view of an electric toothbrush of the second embodiment of this invention.

The first brush part 20 is mounted at the end of the head part 10 remote from the handle. The first brush part 20 is mounted for limited reciprocal motion about a first rotation axis B-B perpendicular to the longitudinal direction A-A. Many suitable ways are known in the art by which the brush part 20 may be so mounted, as are suitable transmission systems between the drive shaft 14 and carrier 20. Bristles 21 extend from the first brush part 20 substantially parallel to axis B-B.

Mounted on the head part 10 adjacent to the first brush part 20 is a second brush part 30, at the end of the head part 10 closest to the handle. Extending from second brush part 30 are second bristles 31 extending substantially parallel to axis B-B, i.e. substantially perpendicular to the longitudinal direction A-A. The second brush part 30 is mounted for limited reciprocal longitudinal motion as follows, and is more clearly shown in FIG. 3.

The second brush part 30 is in the form of a saddle having a longitudinal channel 32 which can sit upon a generally corresponding part 15 of the head part 10, which functions as a rail part. The second brush part 30 is consequently of generally a "C" shaped cross section. The second brush part 30 is also provided with slider parts 33 on its opposite longitudinal sides which fit into corresponding longitudinal slots 16 respectively in opposite sides of head part 10. Slider parts 33 can slide longitudinally along head part 10 within slots 16, and the limits of longitudinal movement of the slider parts 33 is limited by abutment of the longitudinal ends of slider parts 33 against the longitudinal ends of the slots 16.

It will be understood that there are other ways in which the brush part 30 can be mounted for limited reciprocal longitudinal movement on head part 10.

Those skilled in the art will appreciate that the brush part 30 may be assembled with head part 10 in various ways, for example the sides of the brush part 30 adjacent to sliders 33 may be resilient and able to deform outwardly, so that the slider parts 33 can be snap-fitted around head part 15 into slots 16. Parts 10, 20, 30 may be made of resilient plastics materials commonly used in the toothbrush art.

As seen in FIG. 1 second bristles 31 alternate in longitudinal succession between two lengths, a longer length 31A and a shorter length 31B.

In use, the motor is switched on, causing the first brush part 20 to rotate in reciprocal rotary motion. The user then applies the toothbrush head part 10 to the teeth, suitably using the known Bass technique in which the head part 10 is moved reciprocally longitudinally along the line of the teeth. Friction between the second bristles 31 and the teeth cause the second brush part 30 to move reciprocally longitudinally in the opposite direction to which the toothbrush head part 10 is moved, as shown by the arrows in FIGS. 1 and 2, between the limits of movement defined by the longitudinal ends of the slots 16. It is found that reciprocal movement of second brush part 30 with a maximum amplitude in the range 0.5-1.5 mm, typically ca. 0.7 mm between the limits of longitudinal motion is suitable.

Referring to FIGS. 4 to 9 an electric toothbrush 40 comprises a handle 41 which contains inter alia a power supply such as a battery (not shown) and a drive motor (not shown), and a head 42, upon which is mounted a first brush part 43, which is disc-shaped to be driven by the drive motor in rotary motion about a rotation axis A-A passing through the centre of the disc shape of brush part 43 transverse to the head—handle direction, and connected by a transmission means (not shown) to the motor. There is a neck 44, integral with head 42 extending from the handle 41 and connected to the head 42 which internally contains the transmission means. The head 42 is replaceable, being integral with the neck 44, the neck 44 being replaceably connectable to the handle 41 at its end 45 remote from the head 42. A cluster of tufts of bristles 46 is mounted on the first brush part 43, extending from a bristle surface thereof facing generally in a bristle direction parallel to the axis A-A, with their ends closest to the brush part 43 set in the first brush part 43 and their distal ends furthest from the head 42. The bristles 46 are the only oral hygiene parts on the first brush part 43. The rotary motion about axis A-A is oscillatory, i.e. motion involving reciprocal angular displacement about a mean position.

Longitudinally immediately adjacent to first brush part 43 is a second brush part 47, such that the first brush part 43 is furthest from the handle 41, and the second brush part 47 is closer to the handle 41 than the first brush part 43. The second brush part 47 is substantially semi-oval or cresecentic in plan looking down the bristle direction.

Figure 5:
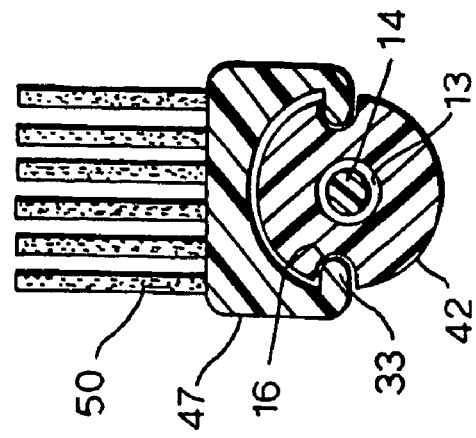
FIG. 5 shows a cross section at line B-B through the head of FIG. 4.
Figure 7:
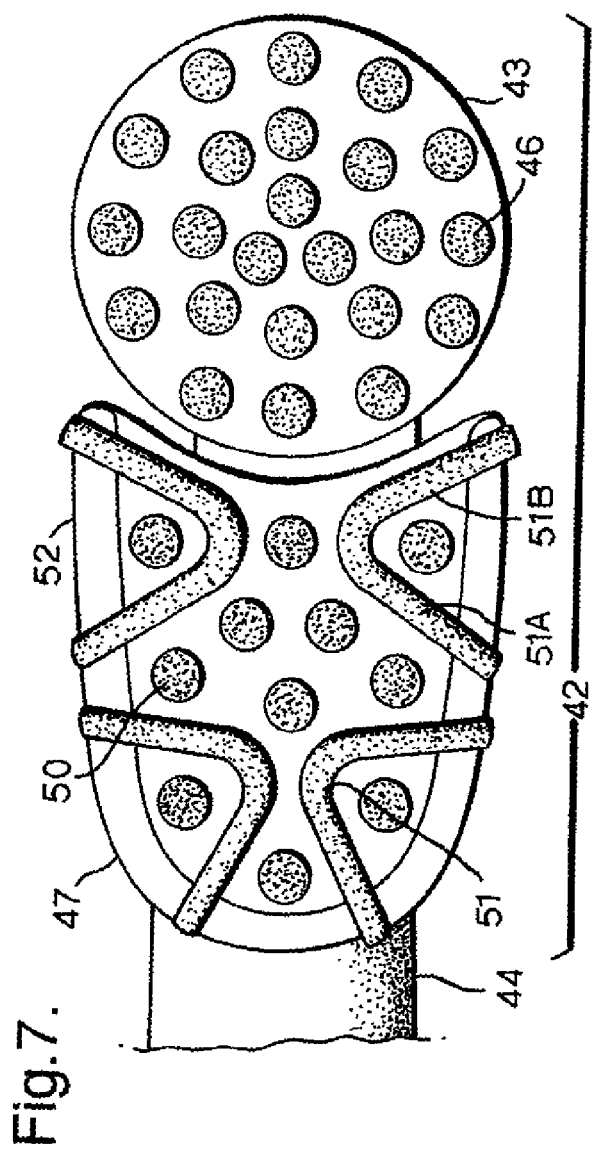
FIG. 7 shows a plan view of the head of FIGS. 4-6.

The second brush part 47 is mounted on the head 42 so as to be capable of limited reciprocal longitudinal motion of a longitudinal amplitude ca. 0.5 mm-1.5 mm, typically ca. 0.7 mm, along the head-handle direction. The overall construction of the second brush part 47 is similar to the second brush part 30 of FIGS. 1-3 and corresponding numbering of parts is used. A cross section through the brush part 47 at line B-B of FIG. 4 is shown in FIG. 5.

The second brush part 47 also has tufts of bristles 50 mounted on its upper surface, the bristles 50 being aligned parallel to the bristles 46 on the first brush part 43. The second brush part 47 also has elastomeric cleaning parts 51 mounted thereon. Each part 51 comprises a pair of elastomeric strips 51A, 51B extending in their length dimension from the second brush part 47, each with a width dimension perpendicular to its length direction, and a thickness dimension perpendicular to both the length and width directions, the thickness dimension being less than the width dimension. The length of the parts 51 is less by ca. 0.2-1 mm than the length of the bristles 110. The pairs of strips 51A, 51B are integrally made, and their width directions converge and meet such that their respective width dimensions form a "V" shape, and so that each part 51 is integrally of a "V" shaped cross section as cut across its length direction, enclosing an angle ca. 60-90°. The "V"'s point inwardly relative to the longitudinal head-handle direction.

Figure 6:
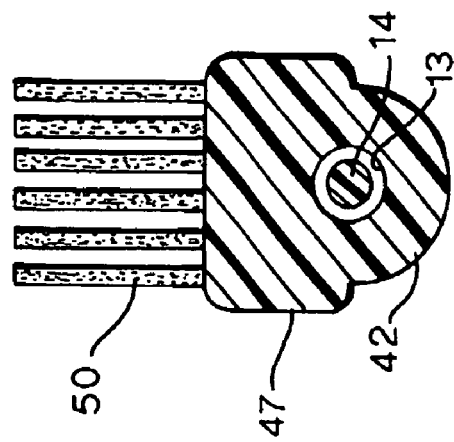
FIG. 6 shows an alternative construction of the head of FIG. 4.

The elastomeric oral hygiene parts 51 are arranged along each of the sideways edges of the second brush part 47. The edges of each of the strips 51A, 51B extend to the edge of the second brush part 47 and slightly beyond. The elastomeric material of the parts 51 is continued as a perimeter extension 52 around the edge of the second brush part 47, and down the sides of the second brush part 47 as projecting elastomeric ridges 53, for example to provide gum massaging parts or a buffer against excessive impact with the oral tissues. it is static and incapable of movement relative to first brush part 43. As shown in FIG. 6 th e FIG. 6 shows a cross section at line B-B of FIG. 4 of an alternative construction of the toothbrush of the second embodiment of this invention. This construction may have an overall appearance and arrangement substantially identical to that shown in FIGS. 4-9 but instead of being reciprocally longitudinally moveable the second brush part 47 is fixed, i.e. second brush part 47 is made integrally with head 42 e.g. by injection moulding.

Figure 10:
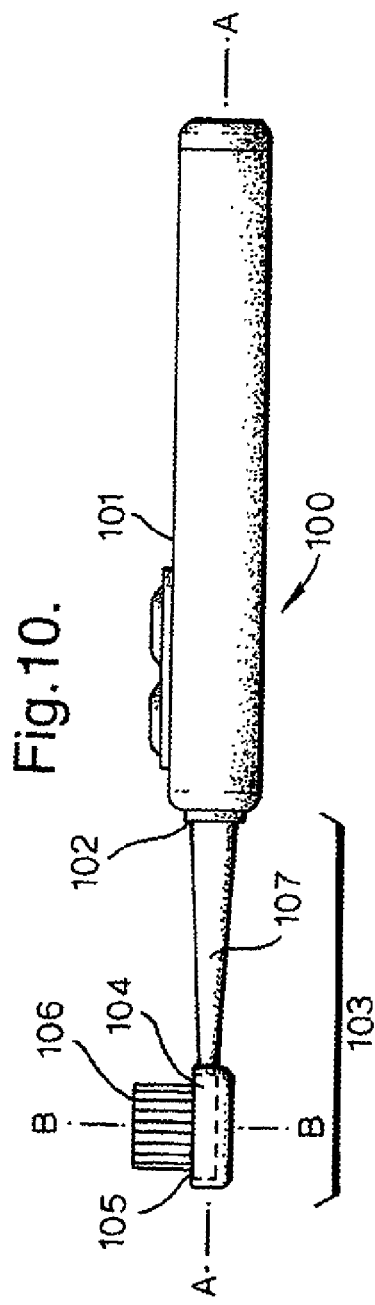
FIG. 10 shows the overall layout of an electric toothbrush of the third embodiment of this invention.
Figure 8:
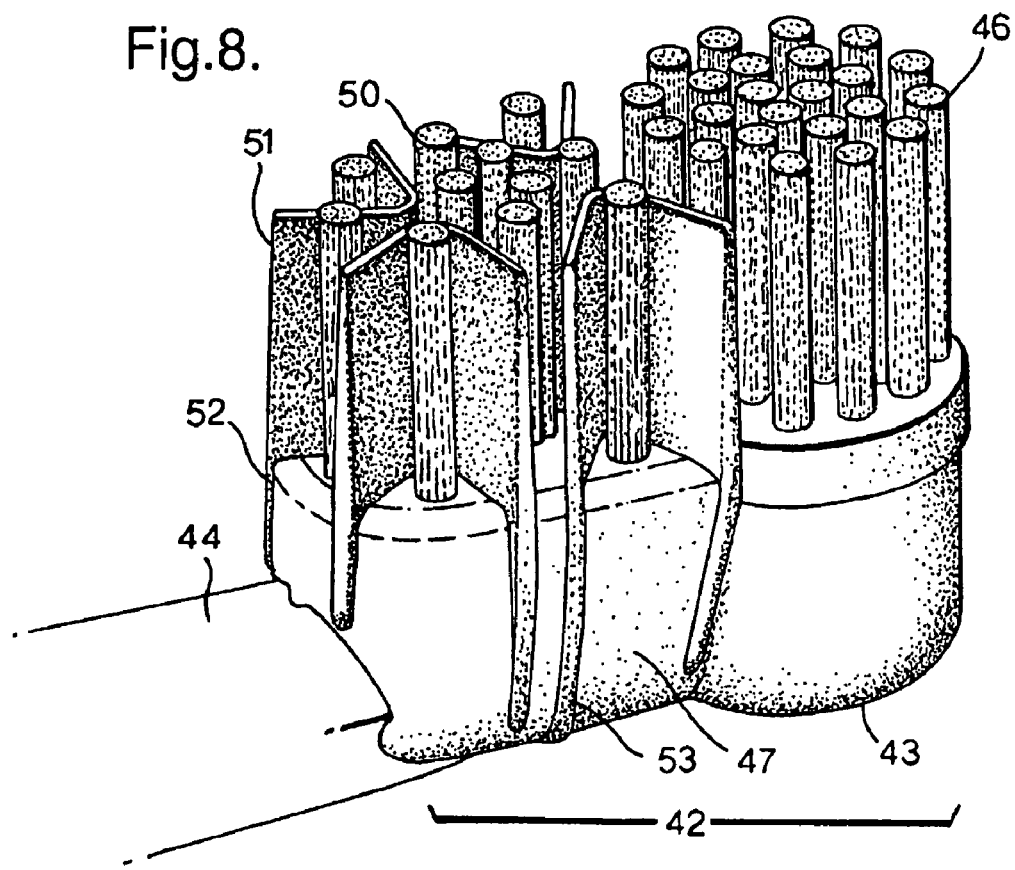
FIG. 8 shows a perspective view of the head of the electric toothbrush of FIGS. 1 to 7.
Figure 9:
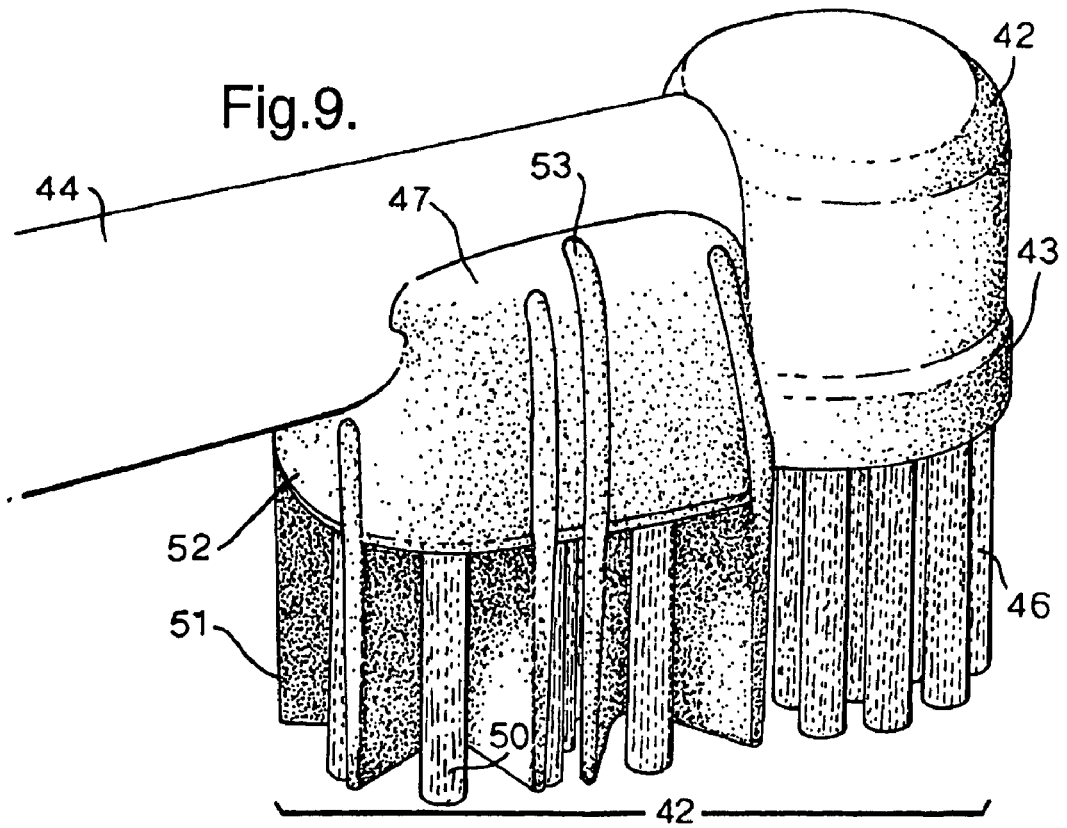
FIG. 9 shows another perspective view of the head of FIGS. 1 to 8.

Referring to FIG. 10 an electric toothbrush is shown overall in side view 100. The toothbrush 100 comprises a handle 101 by which it may be held, and which includes a drive motor, batteries, controls etc. (not shown). The handle 101 is replaceably connected at link 102, suitably a bayonet connection, to a replaceable head part 103. The assembly of handle 101 and head part 103 are disposed along the length direction A-A of the toothbrush 100. In the head part 103 is a brush part 104 mounted to be driven in oscillatory rotary motion around an axis B-B by the motor within handle 101. A conventional transmission mechanism, e.g. a drive shaft running along the head part 103 connects the motor to brush part 104.

From a face 105 of brush part 104 a cluster of oral hygiene parts 106 extend in a direction generally perpendicular to the length A-A. In use the brush part 104 performs an oscillatory, i.e. reversing, rotary motion about an axis of rotation parallel to bristle direction B-B and passing through the centre in plan of the cluster 106, the amplitude of the oscillatory rotary motion being ca. 30° either side of a mean position.

In FIG. 10 the head part 103 is shown as comprising a neck part 107 between the brush part 104 and handle 101. In an alternative construction (not shown) the neck part 107 may be integral with the handle, and the brush part 104 may itself be replaceably connectable to the neck part.

Referring to FIG. 11, a plan view of the cluster 106 is shown, looking down onto the upward facing surface 104 of brush part 105 in the direction B-B. The brush part 105 is circular and the rotation axis B-B of FIG. 1 passes through the centre of brush part 105.

The cluster comprises plural, six being shown, there may be more or less, oral hygiene parts 111 which are seen in section cut across the rotation axis. As shown in FIG. 11 each element 111 itself comprises a pair of rubbery strips 112 the cross section of each strip of which is elongated along a long dimension 'L' which is aligned at a non-zero, non-perpendicular angle to a radius from the axis of rotation and intersecting the strip. The respective long dimensions of the adjacent strips 112 converge, and adjacent edges of strips 112 are joined at edge 113 so that the pair of joined rubbery strips 112 forms the element 111 of unitary "V" or chevron cross section. The elements 111, and consequently the strips 112, are arranged on a circle centred on the rotation axis B-B. In FIG. 11 the points of each of the "V" or chevron shaped sections points radially outwardly from the central rotation axis B-B.

Referring to FIG. 12 similar elements 121 are shown, again each element 121 itself comprising a pair of rubbery strips 122 of which their respective long dimensions converge, and adjacent edges are joined at edge 123 so that the pair of joined rubbery strips 122 forms an element 121 of unitary "V" or chevron cross section cut across the rotation axis B-B. However in FIG. 12 the points of the "V" or chevron points inwardly toward the axis of rotation B-B.

The cross section of each of the strips 112, 122 making up the "V" section elements 111, 121 is elongated in a straight line, and the section has substantially parallel opposite long sides terminating at short edges 114.

As shown the long dimension of the section of each strip 112, 122 is aligned at an angle ca. 45° to radii intersecting the strip.

On the brush part 105 the elastomeric oral hygiene parts 111, 121 are combined in a cluster, centred on the rotation axis, with tufts of bristles 115, 125. The tufts of bristles 115, 125 are arranged in an inner polygon of tufts 115, 125 with a central tuft, and circumferentially between adjacent elastomeric oral hygiene parts 111, 121 there are tufts of bristles 115, 125. The circle of elastomeric oral hygiene parts 111, 121 is in each case the radially outermost of the oral hygiene parts on face 104.

The elastomeric oral hygiene parts 111, 121 extend from the face of the brush part, i.e. in their length direction extending out of the plane of FIGS. 11 and 12 for ca. 10 mm, and the bristles 115, 125 extend to approximately the same length. Typically the long dimension of the section of each strip 112, 122 is ca. 3 mm and the short (thickness) dimension ca. 0.25 mm.

Referring to FIG. 13, a plan view of a face 104 is shown, with radii R radiating from the rotation axis B-B. A plurality of strips 131 of elastomeric material is shown in FIG. 13A arranged on a circle centred on the rotation axis, and FIGS. 13B and 13C respectively show a single strip 111, 121 of the arrangements of FIGS. 11 and 12. Each elastomeric strips 131, and each of the elastomeric strips 112, 122 which make up the elastomeric oral hygiene parts 111, 121, is seen in section cut across the rotation axis and the section is elongated along a long dimension which is aligned at a non-zero, non-perpendicular angle to a radius R intersecting the strip. In each case the angle is ca. 45°.

The invention claimed is:

1. An electric toothbrush comprising a head which is connected to, or replaceably connectable to, a handle which contains an electric motor, to provide a toothbrush having a head-handle longitudinal direction, wherein the head has:
    at least one first brush part bearing oral hygiene parts, said first brush part being driveable by the motor in rotary motion about a first rotation axis generally perpendicular to the longitudinal direction;
    and at least one second brush part bearing oral hygiene parts, said second brush part not being driveable by the motor and being capable of limited reciprocal longitudinal motion;
    wherein the head contains only one first brush part and only one second brush part, the first and second brush parts being relatively longitudinally disposed along the head-handle direction, the first brush part being furthest from the handle, and the second brush part being adjacent to the first brush part and closer to the handle when connected to the toothbrush handle than the first brush part, wherein the second brush part is enabled to perform limited reciprocal motion by means of end-stop abutment parts on respectively the head and on the second brush part, which abut when the second brush part reaches the ends of its limited reciprocal motion to thereby limit the reciprocal motion.

2. The toothbrush according to claim 1 wherein the second brush part has pins or sliders on opposite longitudinal sides which slideably engage in respective longitudinal guides in opposite sides of the head.

3. The toothbrush according to claim 2 wherein the second brush part comprises a saddle of substantially "C" section which can fit around the head and be slideably retained on the head.

4. The toothbrush according to claim 2 wherein the longitudinal guides are slots.

5. The toothbrush according to claim 2 wherein the longitudinal guides are grooves.

6. The toothbrush according to claim 1 wherein both of the first and second brush parts have oral hygiene parts being bristles mounted thereon, extending from a bristle face thereof.

* * * * *